US010159518B2

United States Patent
Holowecky et al.

(10) Patent No.: US 10,159,518 B2
(45) Date of Patent: Dec. 25, 2018

(54) FLEXIBLE OBTURATOR

(71) Applicant: Arthrex, Inc., Naples, FL (US)

(72) Inventors: Allen E. Holowecky, Naples, FL (US); Derek C. Sullivan, Bonita Springs, FL (US); Donald K. Shuler, Naples, FL (US); James J. Guerra, Naples, FL (US)

(73) Assignee: Arthrex, Inc., Naples, FL (US)

( * ) Notice: Subject to any disclaimer, the term of this patent is extended or adjusted under 35 U.S.C. 154(b) by 405 days.

(21) Appl. No.: 14/339,159

(22) Filed: Jul. 23, 2014

(65) Prior Publication Data

US 2015/0032169 A1  Jan. 29, 2015

Related U.S. Application Data

(60) Provisional application No. 61/858,520, filed on Jul. 25, 2013.

(51) Int. Cl.
| | | |
|---|---|---|
| *A61F 2/08* | (2006.01) | |
| *A61B 17/84* | (2006.01) | |
| *A61B 17/02* | (2006.01) | |
| *A61B 17/68* | (2006.01) | |

(52) U.S. Cl.
CPC .......... *A61B 17/842* (2013.01); *A61F 2/0805* (2013.01); *A61B 17/683* (2013.01); *A61B 2017/0225* (2013.01); *A61F 2/0811* (2013.01); *A61F 2002/0852* (2013.01); *A61F 2002/0858* (2013.01); *A61F 2002/0882* (2013.01); *A61F 2002/0888* (2013.01)

(58) Field of Classification Search
CPC ... A61B 17/842; A61B 17/28; A61B 17/0485; A61B 17/0482; A61B 2017/0498; A61F 2/0811; A61F 2002/0852; A61F 2002/0858; A61F 2002/0882; A61F 2002/0888
USPC .......................................... 606/905
See application file for complete search history.

(56) References Cited

U.S. PATENT DOCUMENTS

| | | | | |
|---|---|---|---|---|
| 4,730,615 | A * | 3/1988 | Sutherland | A61B 17/823 24/16 PB |
| 6,423,071 | B1 * | 7/2002 | Lawson | A61B 17/0469 606/103 |
| 9,204,959 | B2 * | 12/2015 | Perriello | A61F 2/0811 |
| 2006/0058892 | A1 * | 3/2006 | Lesh | A61B 17/3468 623/23.72 |
| 2006/0100544 | A1 * | 5/2006 | Ayala | A61M 25/0136 600/585 |
| 2011/0087248 | A1 * | 4/2011 | Steffen | A61B 17/0485 606/148 |
| 2011/0224647 | A1 * | 9/2011 | Lazarus | A61M 1/008 604/506 |

(Continued)

OTHER PUBLICATIONS

Gore Smoother Crucial Tool, Smith & Nephew Product Guide, (2013), p. A-40.

*Primary Examiner* — Matthew J Lawson
(74) *Attorney, Agent, or Firm* — Blank Rome LLP

(57) ABSTRACT

A flexible obturator configured to dilate soft tissue without abrading the adjacent bone surface area. The flexible obturator consists of at least one flexible strand (for example, flexible wire, suture or similar malleable flexible material) that is overmolded with a material that allows the device to bend/flex in multiple planes. The overmolded material has an increasing taper to provide graduated dilation through soft tissue.

12 Claims, 6 Drawing Sheets

(56) References Cited

U.S. PATENT DOCUMENTS

2014/0309689 A1* 10/2014 Sikora .................. A61B 17/683
  606/232
2014/0330307 A1* 11/2014 Steffen ................... A61B 17/28
  606/205

* cited by examiner

FLEXIBLE OBTURATOR

CROSS-REFERENCE TO RELATED APPLICATIONS

This application claims the benefit of U.S. Provisional Application No. 61/858,520, filed Jul. 25, 2013, the disclosure of which is incorporated by reference in its entirety herein.

FIELD OF THE INVENTION

The present invention is directed to surgical instruments and, particularly, to a flexible obturator used in surgical procedures.

BACKGROUND OF THE INVENTION

Dilation of tissue (such as bone or soft tissue) facilitates passing a biologic component (for example, autograft or allograft tissue) around, through, or across bony anatomical structures. One of the instruments employed during arthroscopic or minimally invasive surgery is a cannulated obturator or soft-tissue dilator that is typically provided with a blunt tip and is positioned over a guide pin.

There is a need for a flexible obturator or a soft tissue dilator that confers the surgeon the ability to target tissue adjacent any surface of a bony anatomical structure, such as the coracoid during acromioclavicular (AC) repairs. Also needed is an instrument that allows a surgeon the ability to dilate soft tissue to allow easy graft passage around difficult-to-access areas surrounding bones. The flexible obturator should desirably bend/flex in multiple planes.

SUMMARY OF THE INVENTION

The present invention provides a flexible obturator that is capable of dilating soft tissue without abrading the adjacent bone surface area. The flexible obturator consists of at least one flexible strand (for example, flexible wire, suture or similar malleable flexible material) that is overmolded with a material that allows the device to bend/flex in multiple planes. The overmolded material has an increasing taper to provide graduated dilation through soft tissue.

An exemplary method of surgery with the flexible obturator of the present invention comprises inter alia the steps of: (i) providing a flexible obturator in the vicinity of soft tissue attached to bone or cartilage; (ii) inserting the flexible obturator between the soft tissue and the bone/cartilage; and (iii) shuttling the flexible obturator around the bone/cartilage to dilate the soft tissue and allow subsequent passage/insertion of a graft (for example, allograft).

These and other features and advantages of the invention will be more apparent from the following detailed description that is provided in connection with the accompanying drawings and illustrated exemplary embodiments of the invention.

DETAILED DESCRIPTION OF THE PREFERRED EMBODIMENTS

Figure 1:
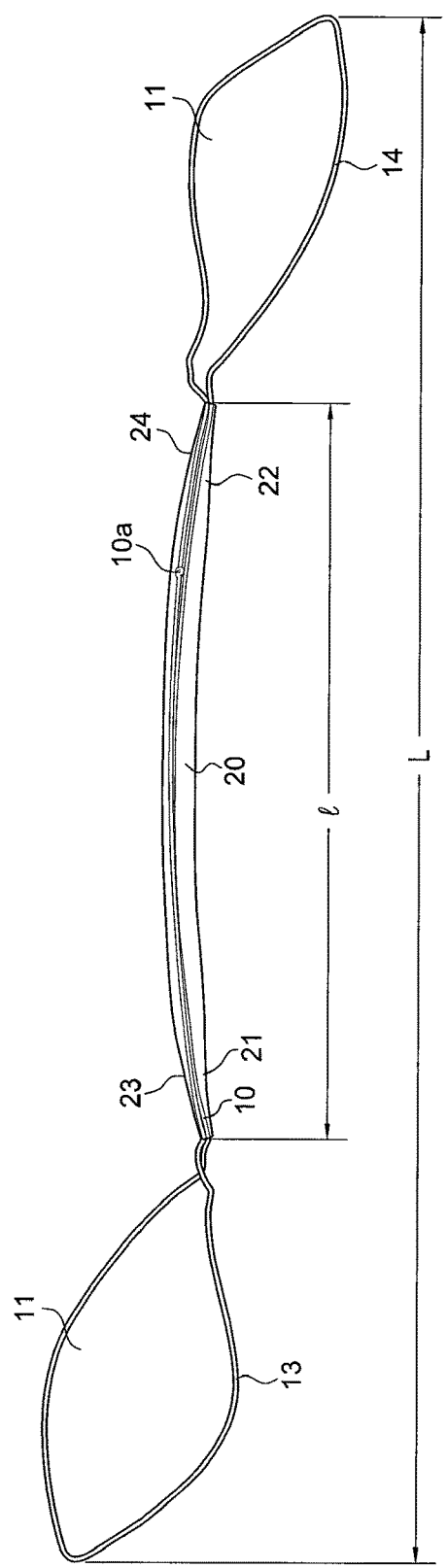
FIG. 1 illustrates an exemplary flexible obturator of the present invention.

The present invention provides a flexible obturator that is capable of dilating soft tissue while maintaining the adjacent bone surface area intact (i.e., without abrading the adjacent bone/cartilage). The flexible obturator is a soft tissue dilator that confers the surgeon the ability to target tissue adjacent any surface of a bony anatomical structure, such as the coracoid during acromioclavicular (AC) repairs. The flexible obturator allows a surgeon the ability to dilate soft tissue to allow easy graft passage around difficult-to-access areas surrounding bones.

The flexible obturator consists of a flexible wire, suture or similar malleable flexible material that is overmolded with a material that allows the device to bend/flex in multiple planes. The overmolded material has an increasing taper to provide graduated dilation through soft tissue. The flexible obturator bends/flexes in multiple planes to facilitate soft tissue dilation while protecting the surrounding bone/cartilage.

Although the flexible obturator of the present invention has particular application to the AC joint, the flexible obturator may be employed in any ligament reconstruction and/or tissue replacement in any kind of joint, and is not limited to the exemplary-only AC repair.

Referring now to the drawings, where like elements are designated by like reference numerals, FIGS. 1-6 illustrate flexible obturator 100 of the present invention which may be positioned between soft tissue and bone or cartilage (for example, the coracoid) at a specific location and following the normal curvature of the bone, and repairs with such flexible obturator 100.

The flexible obturator 100 includes at least one flexible strand 10 such as a flexible wire, suture, tape or similar malleable flexible material that is overmolded with a material 20 that allows the device to bend/flex in multiple planes. The overmolded material 20 has an increasing taper to provide graduated dilation through soft tissue. The flexible obturator 100 bends/flexes in multiple planes to dilate soft tissue while protecting the surrounding bone. The flexible obturator 100 is a smooth graduated dialator for soft tissue dilation which does not reduce any adjacent bone structures.

Flexible obturator 100 may be a single-use disposable and sterile instrument. The at least one flexible strand 10 may be a single strand or may be formed of multiple strands, or may form at least one loop 11 of flexible material (i.e., one or both ends of the flexible strand may be looped to form one or more loops 11). As noted above, the at least one flexible strand 10 may be formed of any material, suture, tape, chain, filaments, yarns, fibrils, loops, knotless suture constructs, etc. The at least one flexible strand 10 may be formed of any fiber, natural or synthetic, absorbable or resorbable, braided or non-braided. The at least one flexible strand 10 may be a FiberWire® suture or multiple FiberWire® sutures.

Molding 20 may be any moldable, flexible material, for example an elastomeric, tissue-compatible material such as silicone, or combination of elastomeric or similar materials (with additional colorants, if desired). Preferably, molding 20 is provided with a taper on at least one side, preferably on both sides/ends of the construct. FIG. 1 illustrates gradual tapers 21, 22 (increasing tapers 21, 22) at ends 23, 24 of the molding 20. Molding 20 extends along a length of the flexible strand, for example, completely surrounding length "l" of the flexible strand 10. In the embodiment shown in FIG. 1, length "l" represents about half the total length "L" of device 100.

In exemplary-only embodiments, the at least one flexible strand 10 is a single strand that forms two loops 11, each loop 11 being provided at each end (i.e., at end 13 and opposite end 14 of the device). The two ends of the strand 10 are brought together to form a knot 10a, for example, which is covered by the molding 20. In additional embodiments, the flexible strand forms only one loop 11 at one end, the other end of the flexible strand remaining un-looped (and covered by the molding 20). In additional embodiments, the flexible strand may form no loop and have a length covered by the molding 20.

In yet additional embodiments, the at least one flexible strand 10 may be in the form of multiple strands of flexible material forming multiple flexible loops at one end, for example, two or more loops 11 located at one end, for example, at end 13. Loops 11, and any additional loops, may be independently-formed loops that are all connected by common region. The construct 100 may also include splices and splice regions formed by splicing one end of the flexible strand 10 within itself, to form loops and/or loop constructs, as desired. In yet additional embodiments, the at least one flexible strand 10 may be in the form of a single strand that branches out in multiple loops 11 (for example, a series of loops 11*a*, 11*b*, etc. as independently-formed loops—not shown) of flexible material. The loops may be all formed of a similar material (same flexible strand material) or may be formed of different materials. The loops allow a graft or tissue (for example, allograft, autograft, artificial tissue, additional suture or fixation devices, etc.) to be connected to the construct 100, i.e., to be passed through and looped over the flexible loops.

Flexible obturator 100 may be employed in any soft tissue reconstruction, for example, graft (ligament, tendon, etc.) reconstruction such as AC joint repair, among many others. Flexible obturator 100 has particular applicability to the AC repair as the coracoid anatomy requires the surgeon to manipulate the graft from medial to lateral and then around the coracoid during the AC repair, step which poses difficulty during the surgical repair. Current AC repairs employ a guide which is a curved instrument (shown as instrument 70 in FIG. 2, for example) to go around the coracoid and allow tissue (for example, biological and non-biological materials such as a graft, allograft, tendon, ligament, etc.) to be pulled around the coracoid. When the graft is pulled, however, the graft gets stuck in the adjacent soft tissue, impeding the procedure. With the flexible obturator 100 of the present invention, and as detailed below, the soft tissue around the coracoid is dilated allowing the graft to be passed easily around the coracoid.

The flexible obturator 100 may be employed in conjunction with various AC reconstruction techniques, for example, the one detailed and described in US Publication 2012/0150203, filed Dec. 8, 2011, entitled "Acromioclavicular Joint Fixation Using Suture Button Construct With Dog Bone-Shaped Button," the disclosure of which is incorporated in its entirety by reference herein.

If desired, the graft can be attached to flexible obturator 100 and then both steps can be conducted at the same time, i.e., dilation of soft tissue and graft passage/insertion can be conducted simultaneously. The flexible obturator 100 may be also hooked to a passing instrument (for example, a passing wire) that has been already passed around the coracoid.

FIGS. 2-6 illustrate exemplary steps of a method of soft tissue reconstruction with the flexible obturator 100 of FIG. 1.

Figure 2:
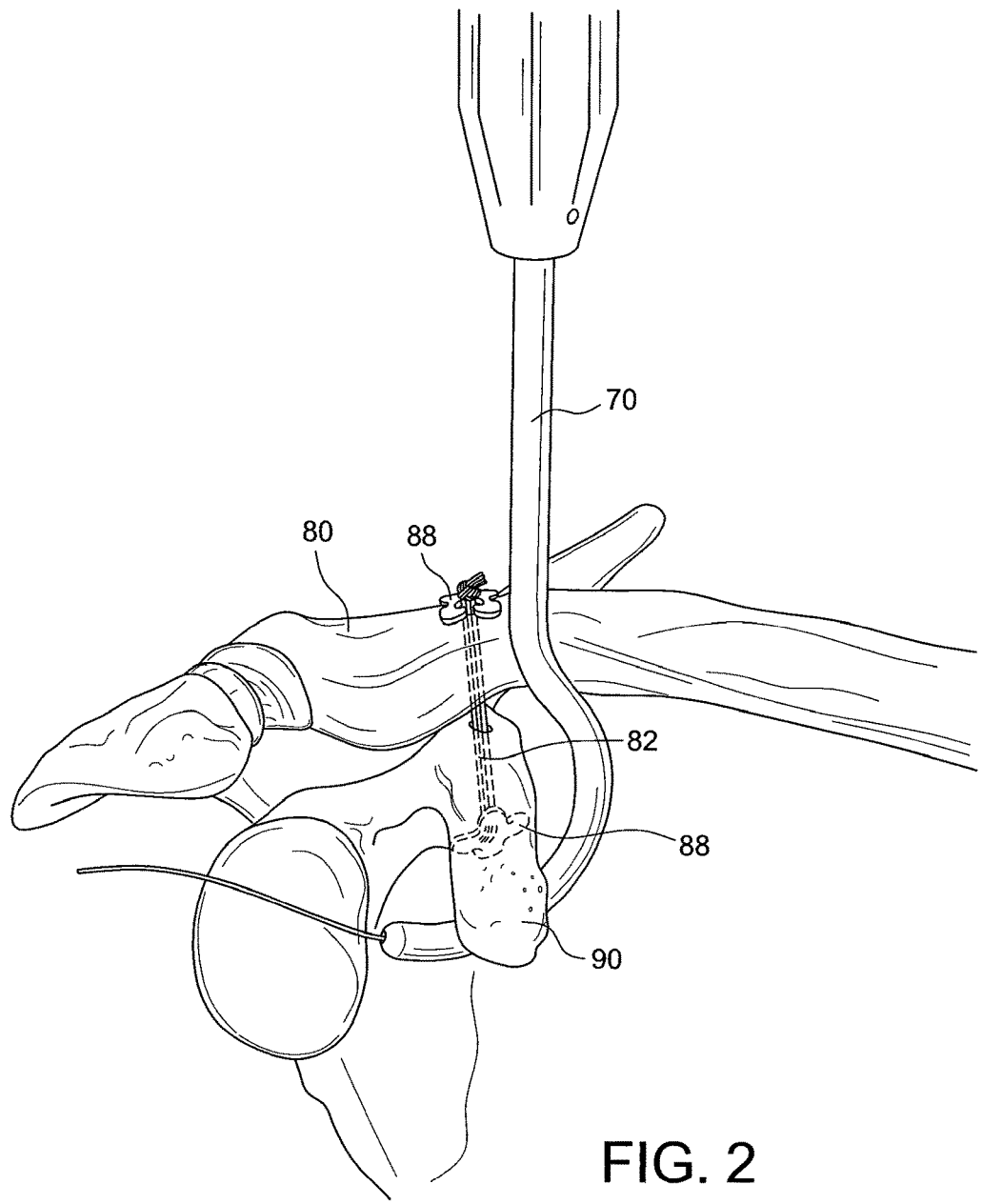
FIGS. 2-6 illustrate subsequent steps of an exemplary surgical technique with the flexible obturator of FIG. 1.

FIG. 2: Perform desired AC reconstruction (for example, by employing dog bone buttons 88 and a suture loop construct 82 extending between the two buttons, as detailed in US Publication 2012/0150203, to secure clavicle 80 to coracoid 90). Pass an instrument 70 from medial to lateral around the coracoid 90. An exemplary curved guide instrument 70 is used in this example.

Figure 3:
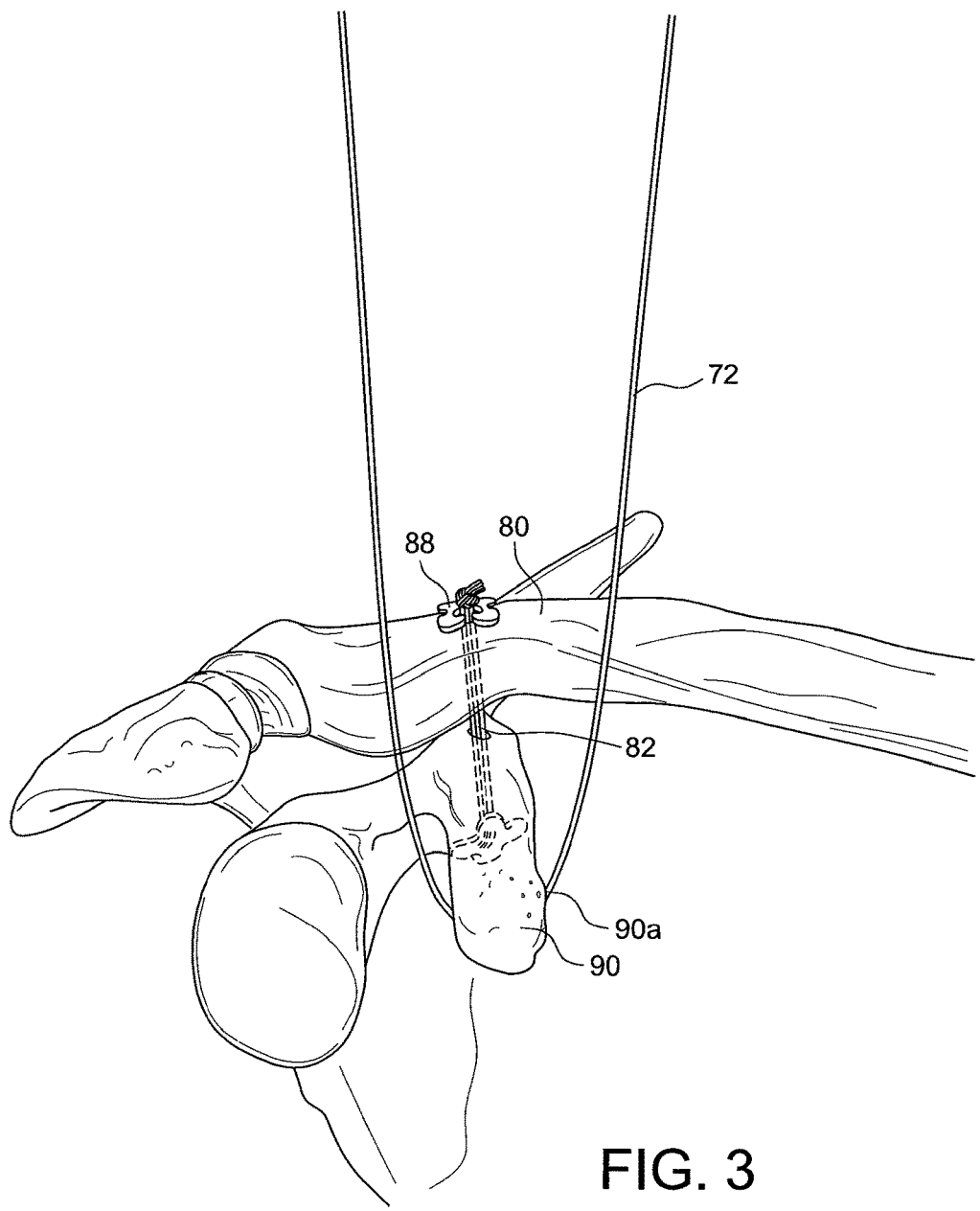

FIG. 3: Use the instrument 70 to pass a wire or suture 72 around area 90*a* of the coracoid 90, i.e., right around the bone surface of coracoid 90.

Figure 4:
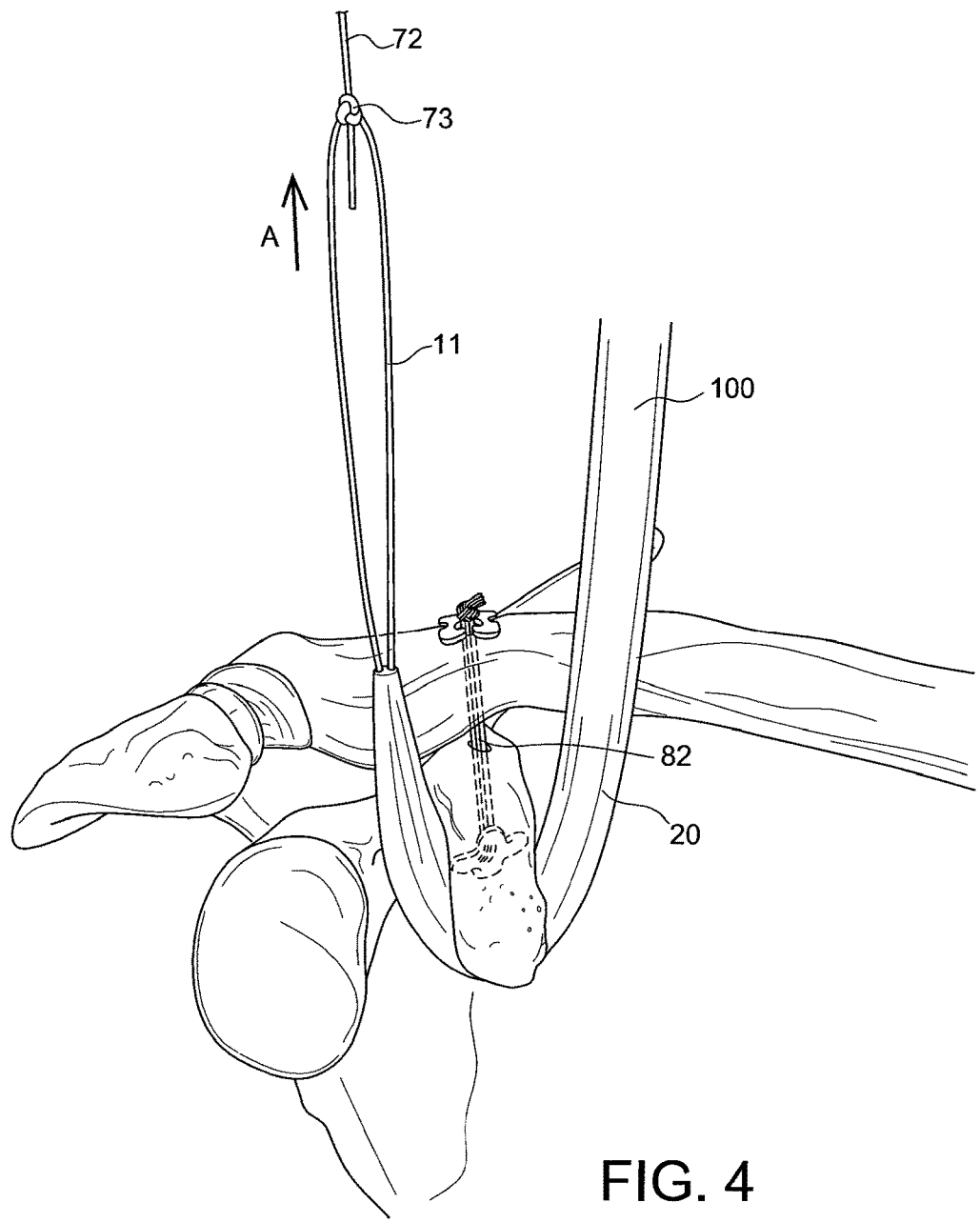

FIG. 4: Secure the wire or suture 72 to the flexible obturator 100 (by tying a knot 73, for example) and shuttle it around area 90*a* of the coracoid 90 to dilate the soft tissue that is adjacent and/or contacts bone area 90*a* of coracoid 90. Pulling the flexible obturator 100 in the direction of arrow A of FIG. 4 allows the soft tissue in area 90*a* of the coracoid 90 to distance itself from the coracoid 90 (i.e., to dilate the anatomical soft tissue). The wire or suture 72 can be secured to the flexible obturator 100 by tying the two together, folding the suture, integrating a FiberLink™ with the dilator, or splicing the sutures together.

Figure 5:
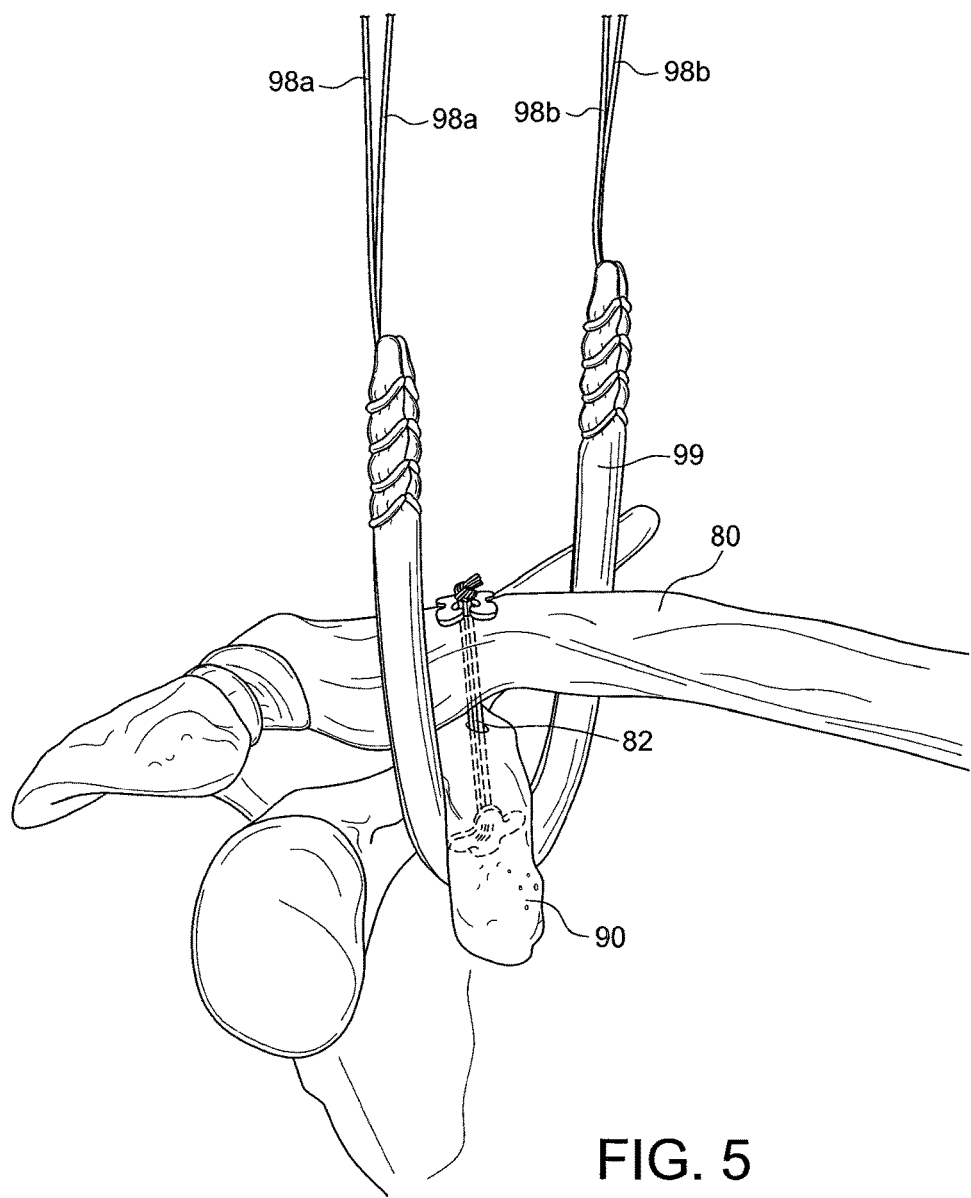
Figure 6:
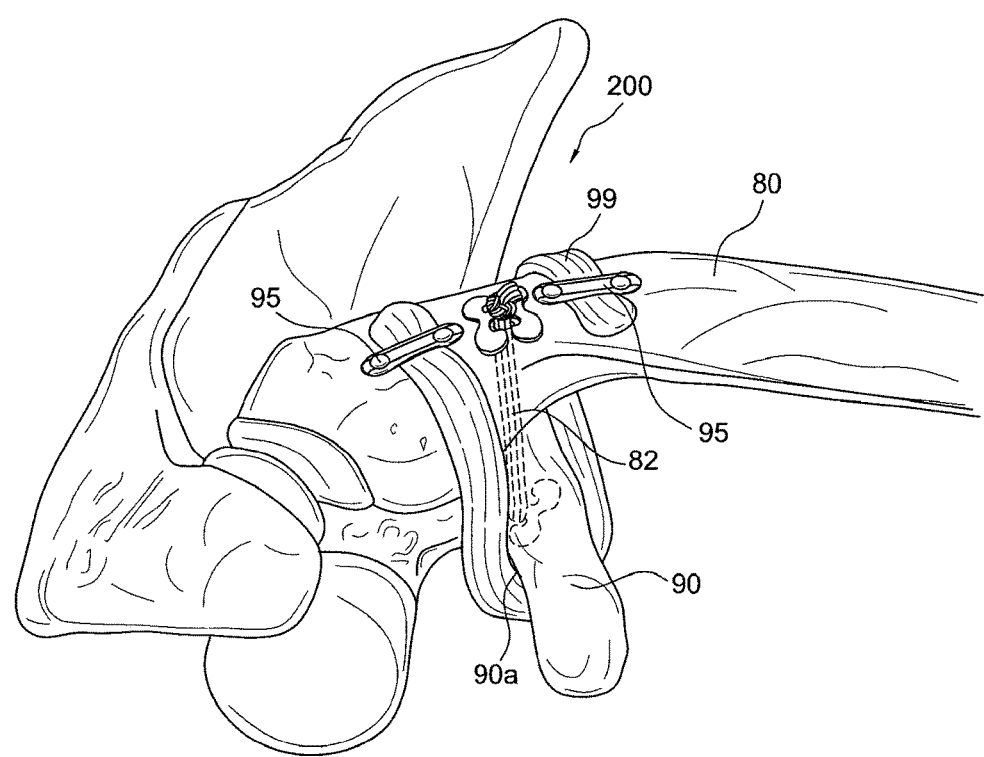

FIGS. 5 and 6: Attach the suture limbs 98*a*, 98*b* from tissue 99 (for example, allograft 99) to the flexible obturator 100 and shuttle around the coracoid 90 (i.e., within area 90*a* of the coracoid). Graft 99 is secured to clavicle 80 and around coracoid 90 with fixation devices (for example, fixation devices 95) to obtain final repair 200 of FIG. 6.

The flexible strand 10 forming construct 100 may be a high-strength suture, such as an ultrahigh molecular weight polyethylene (UHMWPE) suture. Alternatively, the high strength suture may be a FiberWire® suture, which is disclosed and claimed in U.S. Pat. No. 6,716,234, the entire disclosure of which is incorporated herein by reference in its entirety herewith. FiberWire® suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material. The preferred FiberWire® suture includes a core within a hollow braided construct, the core being a twisted yarn of UHMWPE.

The flexible strand 10 of the present invention may also be formed of a stiff material, or combination of stiff and flexible materials, depending on the intended application. The strands may be also coated and/or provided in different colors.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting.

What is claimed is:

1. A surgical flexible obturator for dilating tissue, the obturator comprising of:
   at least one flexible strand having at least one closed loop at one end and a length adjacent the at least one closed loop; and
   an overmolded material surrounding at least a part of the length of the at least one flexible strand, the overmolded material being adjacent to and ending at the at least one loop at one end of the flexible strand and the overnolded material having at least one increasing taper along the length of the flexible strand,
   wherein the at least one flexible strand is a wire, a suture, a suture tape, a suture chain, a filament, a yarn, or a fibril.

2. The surgical obturator of claim 1, wherein the overmolded material bends in multiple planes relative to its longitudinal axis.

3. The surgical obturator of claim 1, wherein the obturator is a single use disposable instrument.

4. The surgical obturator of claim 1, wherein the at least one flexible strand is formed of a plurality of braided multi-filament yarns formed of ultrahigh molecular weight polyethylene.

5. The surgical obturator of claim 1, wherein the at least one flexible strand comprises resorbable material.

6. The surgical obturator of claim 1, wherein the overmolded material is formed of an elastomer, silicon, or combinations of elastomers and silicon.

7. The surgical obturator of claim 1, wherein ends of the at least one flexible strand are brought together in a knot and wherein the overmolded material surrounds the knot.

8. The surgical obturator of claim 1, wherein the overmolded material has another increasing taper to provide graduated dilation through the tissue.

9. A surgical flexible obturator for dilating tissue, comprising:
   at least one flexible strand having a total length including at least an overmolded length and at least one loop; and
   an overmolded flexible material surrounding the overmolded length of the at least one flexible strand, the overmolded length being at least about half the total length of the flexible strand, the overmolded flexible material being adjacent to and ending at the at least one loop, and the at least one loop of the at least one flexible strand being outside of the overmolded flexible material,
   wherein the overmolded flexible material is bendable relative to a longitudinal axis thereof.

10. The surgical obturator of claim 9, wherein the at least one flexible strand has a second loop opposite the at least one loop, the second loop is outside of the overmolded flexible material such that the overmolded flexible material is located between the loops.

11. The surgical obturator of claim 9, wherein the overmolded flexible material has an increasing taper along the length of the flexible strand.

12. The surgical obturator of claim 9, wherein the at least one flexible strand is a suture.

* * * * *